United States Patent
Russo et al.

(10) Patent No.: US 9,974,548 B2
(45) Date of Patent: May 22, 2018

(54) SURGICAL INSTRUMENT FOR HARVESTING BONE

(71) Applicant: Russo Surgical Tools, LLC, Grand Rapids, MI (US)

(72) Inventors: Scott S. Russo, Grand Rapids, MI (US); Jeremy S. Russo, Grand Rapids, MI (US)

(73) Assignee: Russo Surgical Tools, LLC, Grand Rapids, MI (US)

( * ) Notice: Subject to any disclaimer, the term of this patent is extended or adjusted under 35 U.S.C. 154(b) by 308 days.

(21) Appl. No.: 14/848,893

(22) Filed: Sep. 9, 2015

(65) Prior Publication Data

US 2016/0066929 A1     Mar. 10, 2016

Related U.S. Application Data

(60) Provisional application No. 62/048,116, filed on Sep. 9, 2014.

(51) Int. Cl.
*A61B 17/00* (2006.01)
*A61B 17/16* (2006.01)

(52) U.S. Cl.
CPC ...... *A61B 17/1635* (2013.01); *A61B 17/1604* (2013.01); *A61B 17/1615* (2013.01)

(58) Field of Classification Search
CPC ........................................ A61B 7/16–17/1697
See application file for complete search history.

(56) References Cited

U.S. PATENT DOCUMENTS

| | | | |
|---|---|---|---|
| 13,901 A | 12/1855 | Chapman | |
| 86,741 A | 2/1869 | Dutton | |
| 117,839 A | 8/1871 | Watt | |
| 1,015,461 A | 2/1912 | Vichek | |
| 1,991,267 A | 2/1935 | Waldron et al. | |
| 2,876,777 A | 3/1959 | Kees, Jr. | |
| 3,512,519 A * | 5/1970 | Hall | A61B 10/02 30/278 |
| 4,203,444 A | 5/1980 | Bonnell et al. | |
| 4,700,702 A | 10/1987 | Nilsson | |
| 4,733,663 A | 3/1988 | Farley | |
| 5,183,053 A * | 2/1993 | Yeh | A61B 10/00 600/567 |
| 5,186,178 A * | 2/1993 | Yeh | A61B 17/32053 600/567 |
| 5,507,765 A * | 4/1996 | Mott | A61B 10/02 600/567 |

(Continued)

OTHER PUBLICATIONS http://www.rtix.com/products/spine/lateral/lateral-fusion-disc-prep-set; Copyright 2015, RTI Surgical, Inc., 1 page, dated Jan. 7, 2015.

*Primary Examiner* — Matthew Lawson
(74) *Attorney, Agent, or Firm* — Price Heneveld LLP

(57) ABSTRACT

A bone or tissue-cutting instrument for use with a manual handle or with a powered surgical tool includes an elongated shaft and a cutting head portion of a distal end of the shaft. The cutting head portion includes an annular arcuate blade located at the distal-most end of the cutting head portion for cutting or shaving adjacent tissue or bone. The cutting head portion may also include a distal opening defined by the arcuate blade and a proximal opening with a central passage therebetween for collecting and transferring cut bone or tissue cut by the arcuate blade.

19 Claims, 12 Drawing Sheets

(56) References Cited

U.S. PATENT DOCUMENTS

| | | | |
|---|---|---|---|
| 5,536,266 A | 7/1996 | Young et al. | |
| 5,570,700 A * | 11/1996 | Vogeler | A61B 10/02 600/567 |
| 5,571,106 A | 11/1996 | Coufal et al. | |
| 5,620,458 A | 4/1997 | Green et al. | |
| 5,674,235 A | 10/1997 | Parisi | |
| 5,681,337 A | 10/1997 | Bray, Jr. | |
| 5,683,406 A | 11/1997 | Altobelli et al. | |
| 5,725,531 A | 3/1998 | Shapiro | |
| 5,843,110 A | 12/1998 | Dross et al. | |
| 5,857,995 A * | 1/1999 | Thomas | A61B 17/1615 604/22 |
| 5,891,149 A | 4/1999 | Young et al. | |
| 6,030,400 A | 2/2000 | Johnson | |
| 6,110,177 A | 8/2000 | Ebner et al. | |
| 6,217,598 B1 | 4/2001 | Berman et al. | |
| 6,398,793 B1 | 6/2002 | McGuire | |
| 6,425,920 B1 | 7/2002 | Hamada | |
| 6,562,055 B2 | 5/2003 | Walen | |
| D479,605 S | 9/2003 | Ripich et al. | |
| 6,755,837 B2 | 6/2004 | Ebner | |
| D494,272 S | 8/2004 | Ripich et al. | |
| 6,840,941 B2 | 1/2005 | Rogers et al. | |
| 6,949,108 B2 | 9/2005 | Holmes | |
| 8,529,568 B2 | 9/2013 | Bouadi | |
| 2003/0158603 A1 | 8/2003 | Ebner | |
| 2005/0075642 A1 | 4/2005 | Felt et al. | |
| 2005/0090829 A1 | 4/2005 | Martz et al. | |
| 2006/0064102 A1 | 3/2006 | Ebner | |
| 2006/0111722 A1* | 5/2006 | Bouadi | A61B 17/1604 606/79 |
| 2006/0212060 A1 | 9/2006 | Hacker et al. | |
| 2007/0055264 A1 | 3/2007 | Parmigiani | |
| 2007/0208348 A1 | 9/2007 | Parmigiani | |
| 2008/0208194 A1 | 8/2008 | Bickenbach | |
| 2009/0054898 A1 | 2/2009 | Gleason | |
| 2009/0264888 A1* | 10/2009 | Neumeyer | A61B 17/1617 606/80 |
| 2011/0046652 A1 | 2/2011 | Rehnke et al. | |
| 2011/0319899 A1 | 12/2011 | O'Neil et al. | |
| 2012/0029546 A1 | 2/2012 | Robertson | |
| 2013/0238006 A1 | 9/2013 | O'Neil et al. | |
| 2014/0065573 A1* | 3/2014 | Wang | A61C 8/0089 433/166 |
| 2014/0088599 A1 | 3/2014 | Russo et al. | |

* cited by examiner

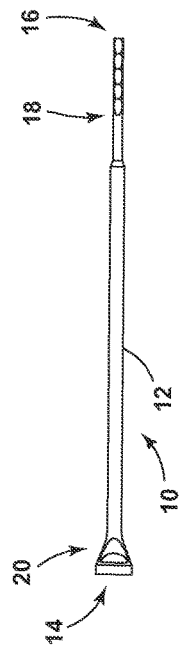
FIG. 2
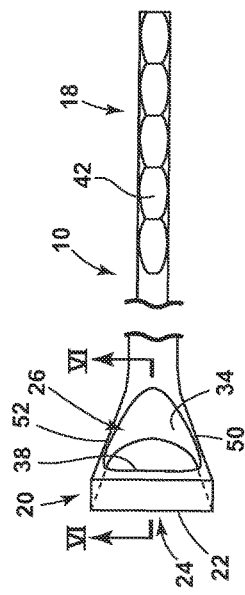
FIG. 5
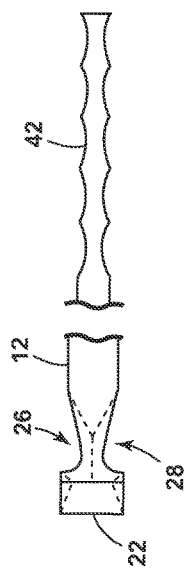
FIG. 3
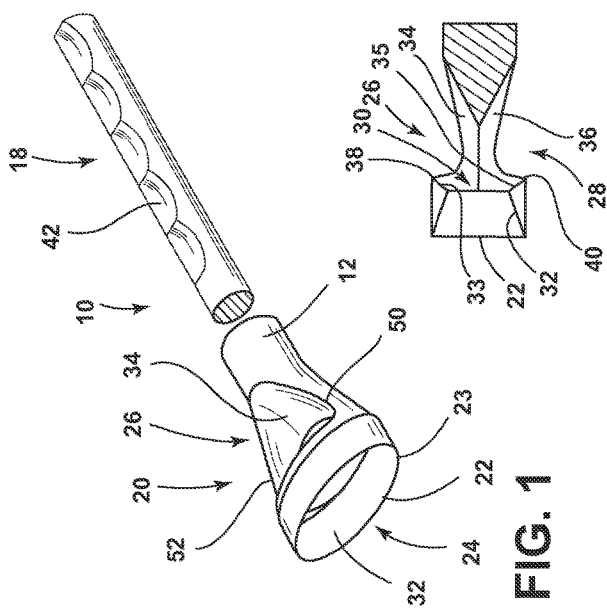
FIG. 1
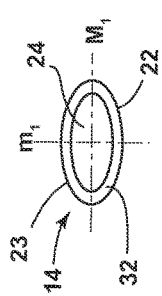
FIG. 6
FIG. 4

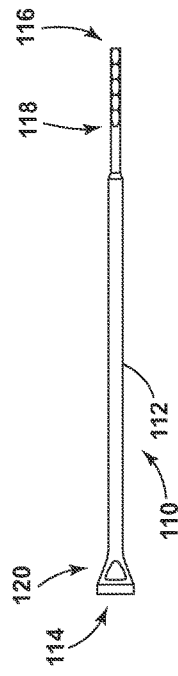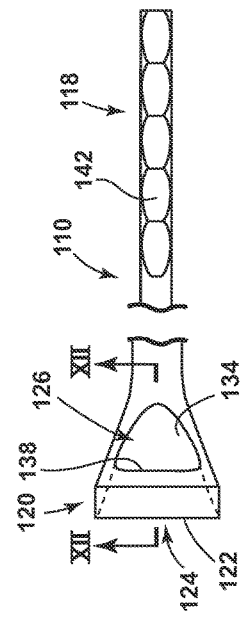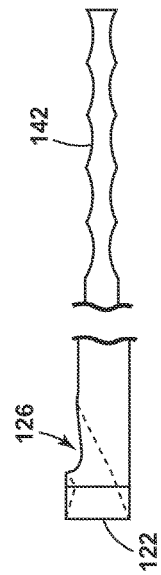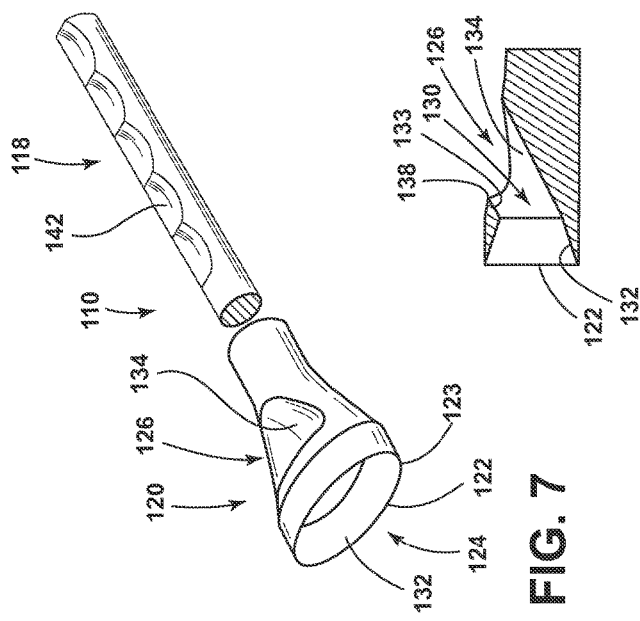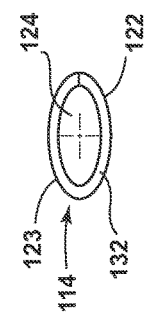

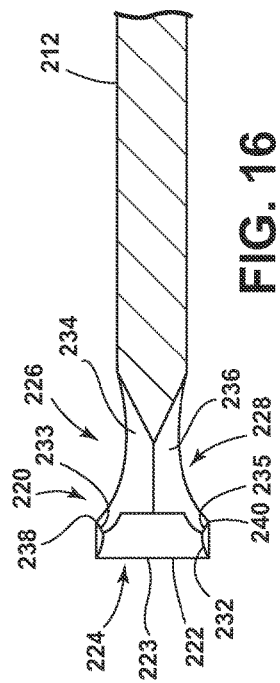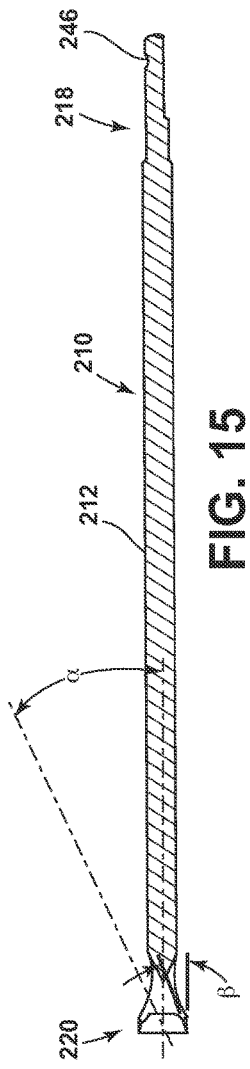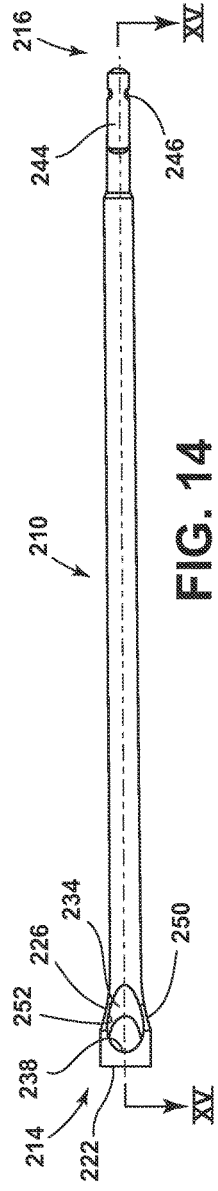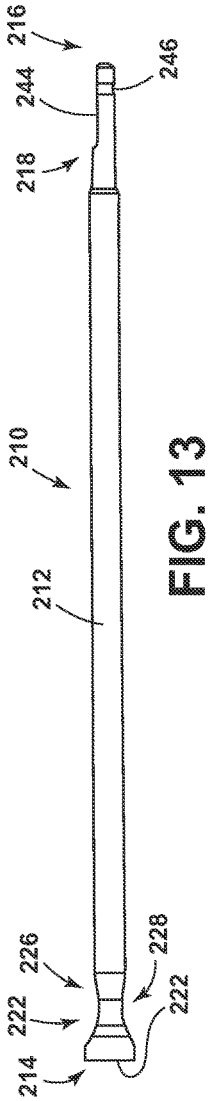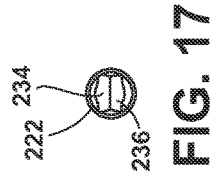

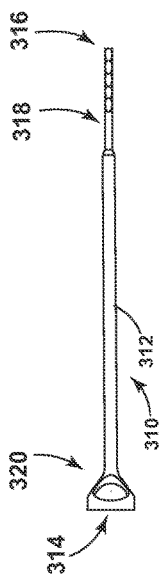
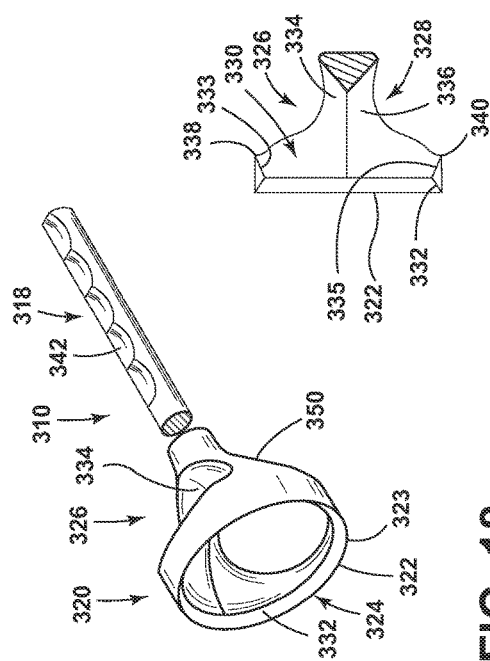
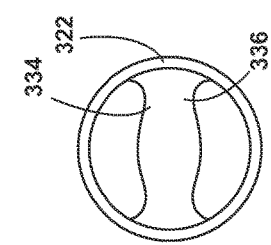
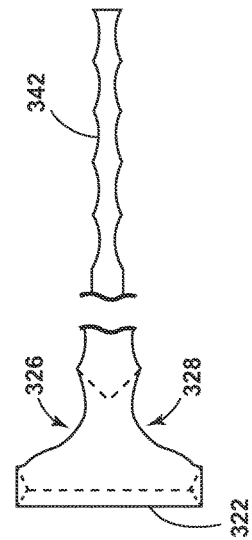
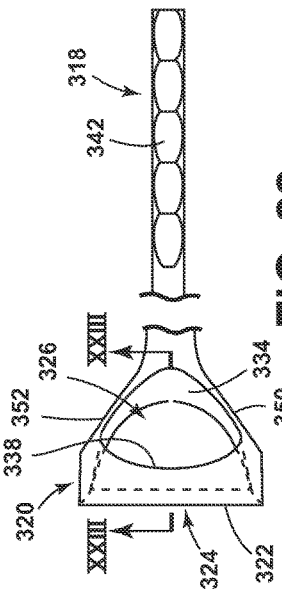

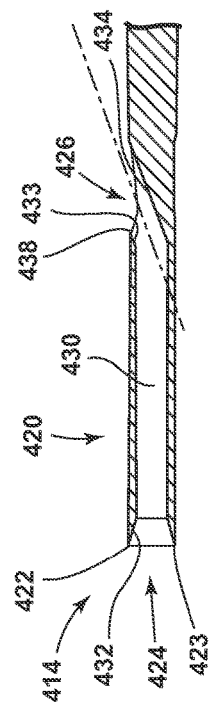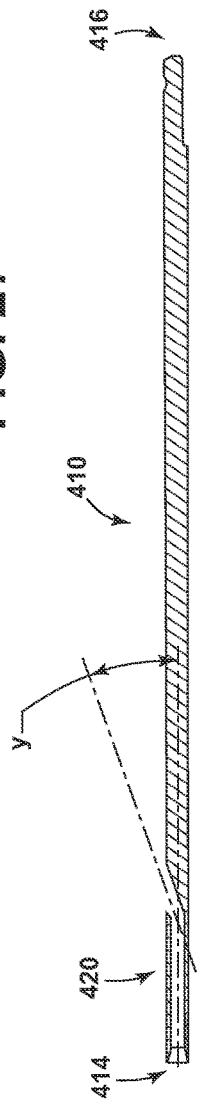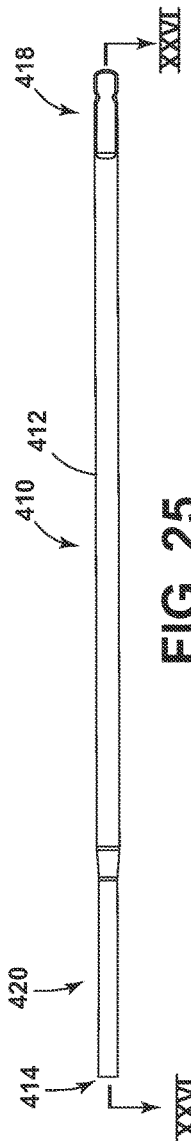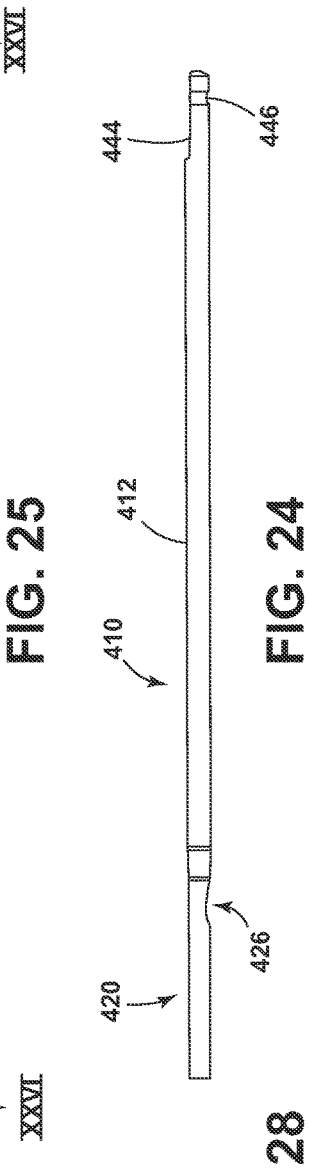

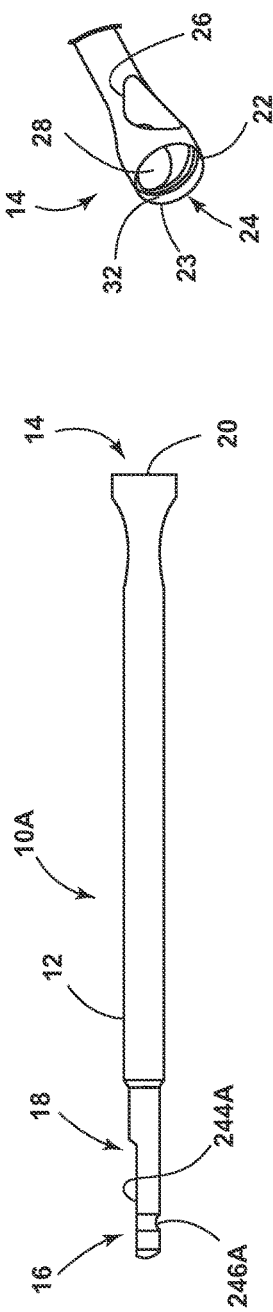
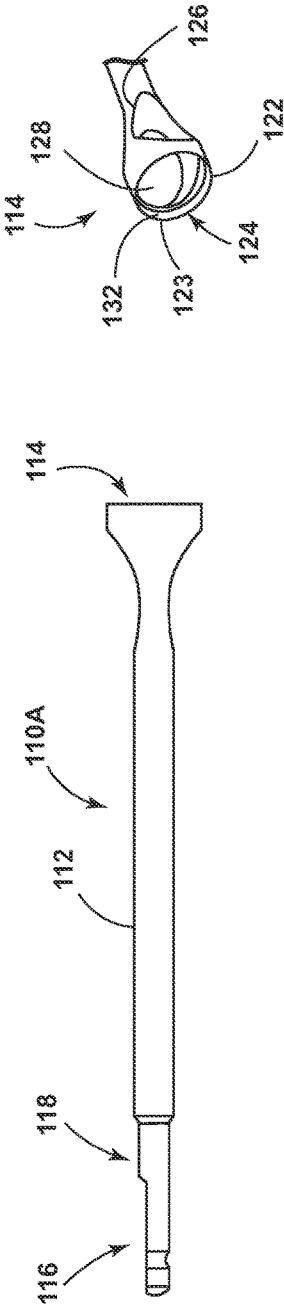
FIG. 29A  FIG. 29B  FIG. 30A  FIG. 30B

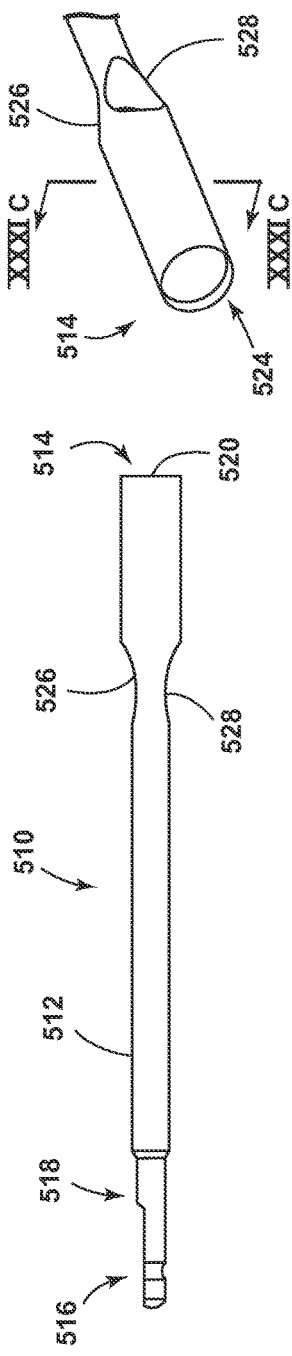
FIG. 31A
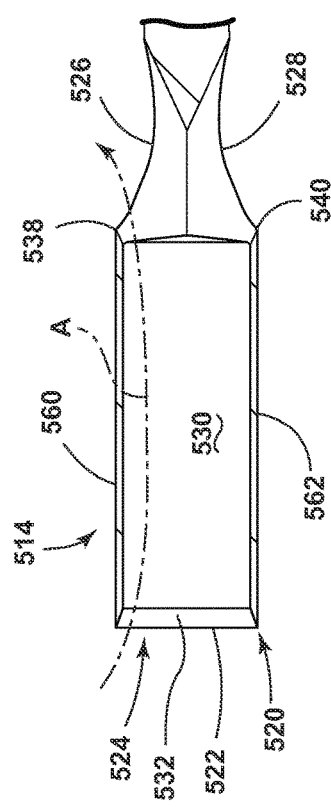
FIG. 31B
FIG. 31C

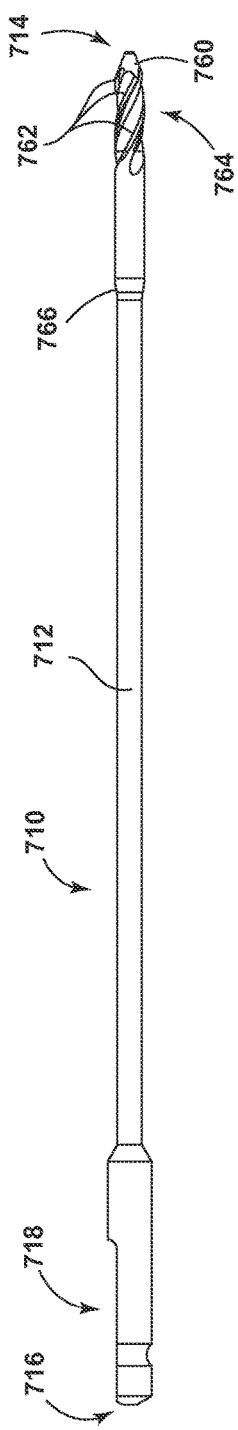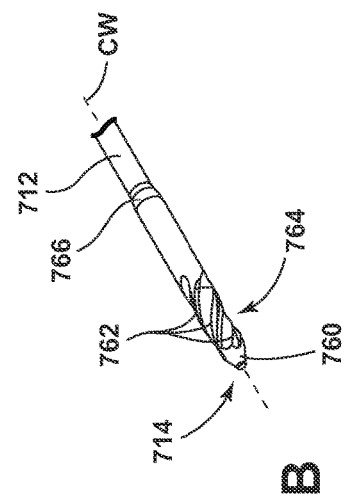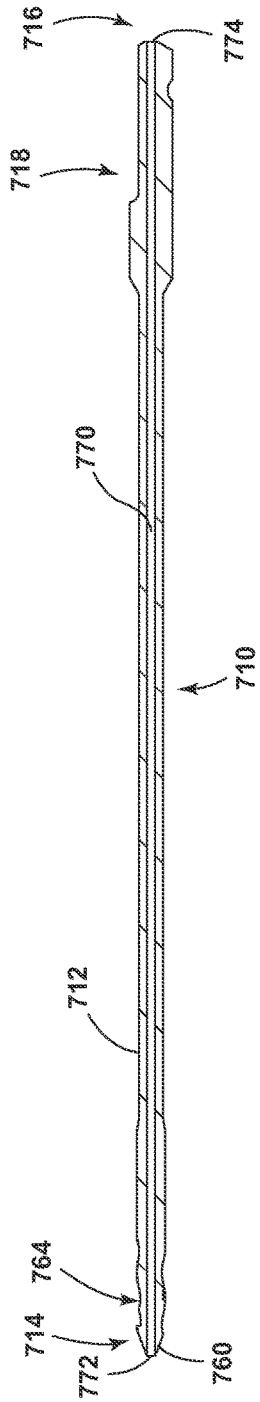
FIG. 33A
FIG. 33B
FIG. 33C

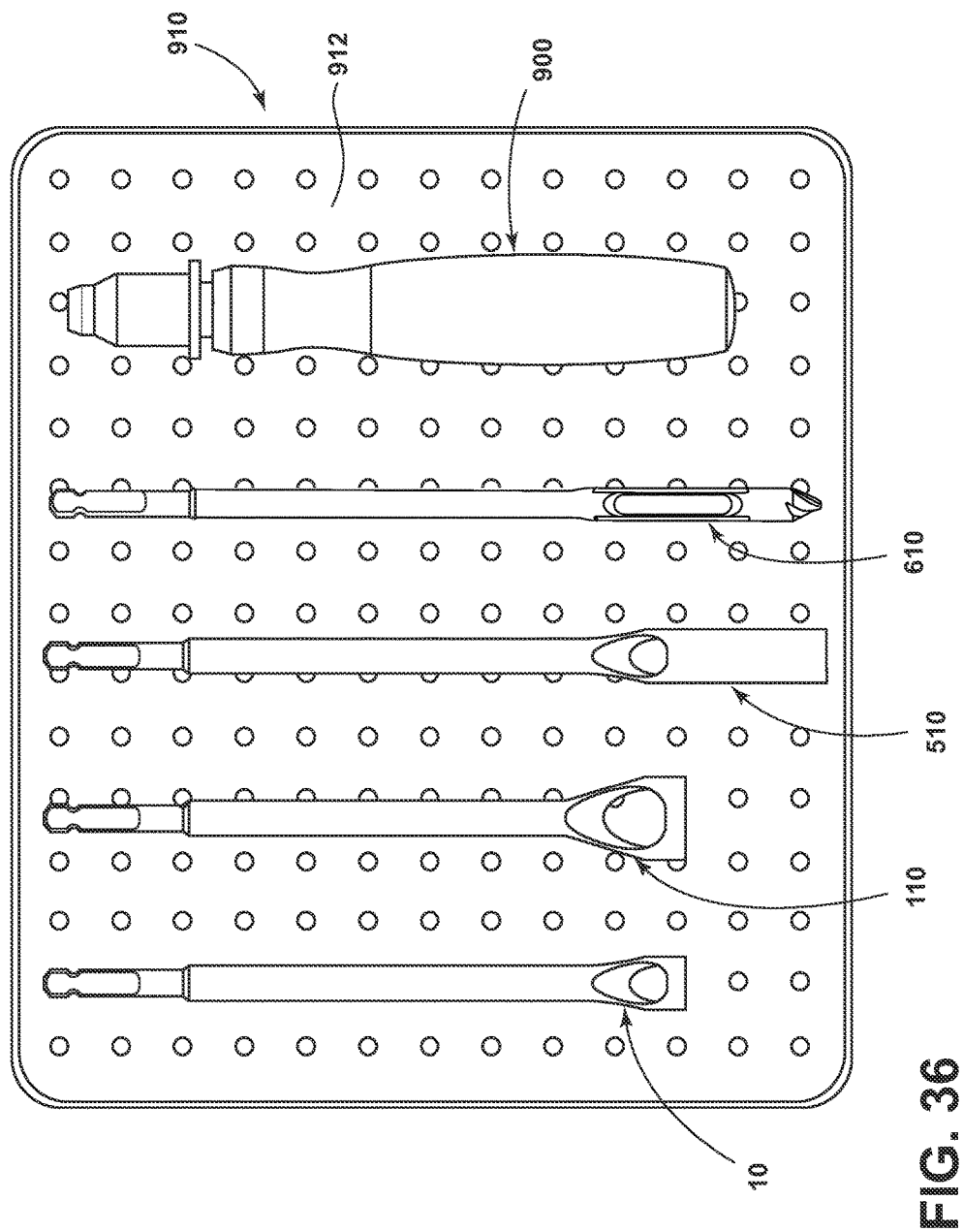

SURGICAL INSTRUMENT FOR HARVESTING BONE

CROSS REFERENCE TO RELATED APPLICATION

This present application claims the benefit of United States Provisional Application No. 62/048,116 entitled "SURGICAL INSTRUMENT FOR HARVESTING BONE" filed on Sep. 9, 2014, the entire contents of which are incorporated by reference.

FIELD OF THE INVENTION

This invention relates generally to a surgical instrument for cutting or shaving bone or tissue, and, more particularly, to a bone or tissue-cutting instrument configured for attachment to a handle or surgical power tool.

BACKGROUND OF THE INVENTION

Tools for cutting, shaving, or contouring bone or other tissue are known in the art, such as chisels, ronguers, rasps, curettes, osteotomes, gouges, and the like. Powered cutting devices, such as oscillating micro surgical saws and surgical drill/burr power tools are known in the art. Various cutting attachments for such tools are known, such as drill bits, burrs, and cutting blades. The cutting attachments for these powered medical devices are generally designed with a proximal shank section that connects to the motor-driven surgical device, and a distal cutting portion. Although these cutting attachments effectively cut bone and in some versions may remove bone fragments, it would be desirable to be able to have a tool that would cut or shave and permit the collection or harvesting of bone fragments in a more efficient and effective manner which could be used manually or attached to such a medical device.

SUMMARY OF THE INVENTION

In one form of the present invention, a surgical instrument for cutting or shaving bone or tissue from a patient's body for autologous graft purposes, as well as for reshaping or contouring orthopedic areas in the spine and musculoskeletal system is provided. The instrument may include an elongated shaft portion having proximal and distal ends with a cutting head at the distal end of the shaft for cutting bone or tissue. The instrument may include a shank portion configured to matingly engage with a handle or a power tool for actuating the instrument. The body of the cutting head includes an annular arcuate blade at a distal end of the cutting head body which defines a distal opening in the cutting head body. The distal opening lies substantially in a plane that is transverse to the longitudinal axis, and in some forms, that plane is perpendicular to the longitudinal axis of the tool, and the distal opening is preferably centered about the longitudinal axis. A proximal opening is located proximally of the distal arcuate blade, and the distal and proximal openings are connected via a central channel that terminates at the proximal and distal openings to allow cut bone or tissue to pass through one opening to the other. In some forms, the proximal opening is disposed on a superior portion of the cutting head body.

The cutting head may have a variety of configurations. In some forms, the arcuate blade of the cutting head has an elliptical configuration, whereas in others the blade has a circular configuration. However, other shapes may be used. The central channel between the distal and proximal openings preferably includes an interior surface portion of the central channel that is inclined with respect to the longitudinal axis of the tool and terminates at the proximal opening for guiding cut bone or tissue along the interior surface portion. The cutting head may include a second proximal opening located proximally of the distal arcuate blade that is connected to the distal opening via the central channel such that the cut bone or tissue may pass through the channel and through either or both of the proximal openings. In this form, the central channel may include interior surface portions that are inclined with respect to the longitudinal axis and diverge apart from one another as they extend proximally and terminate respectively at the proximal openings for guiding cut bone or tissue along the interior surface portions. The inclined surface portion or portions may take a variety of inclinations, but are preferably inclined at a range of between 15 and 45 degrees with respect to the longitudinal axis. In some forms, the proximal openings are located opposite from one another and spaced substantially equidistant from the longitudinal tool axis.

The proximal opening or openings may include a sharpened edge portion for cutting bone or tissue. Preferably, the sharpened edge portion is oriented to cut adjacent tissue or bone when the tool is shifted proximally. In this manner, the arcuate blade at the distal end is configured to cut tissue or bone when the tool is shifted distally along an adjacent tissue or bone, and the sharpened edge portion of the proximal opening is configured to cut tissue or bone when the tool is shifted proximally. Such a configuration is particularly advantageous to shave bone when used in a reciprocating motion, such as with a reciprocating power tool.

In some forms, the cutting head portion is enlarged relative to the shaft portion. In particular, the annular arcuate blade and the shaft portion each have a diameter and the annular arcuate blade diameter is larger than the shaft portion diameter. However, in other forms, the cutting head portion may be of substantially the same size to the shaft or even smaller than the shaft portion diameter.

One aspect of the present invention includes a surgical instrument for cutting bone or other tissue which includes a shaft portion having proximal and distal ends and a longitudinal axis extending between the proximal and distal ends. A cutting head portion is disposed at the distal end of the shaft portion having an arcuate blade at a distal-most end of the cutting head portion which defines a distal opening that lies substantially in a plane that is transverse to the longitudinal axis. A proximal opening is disposed in the cutting head portion and located proximally of the arcuate blade. A central channel connects the proximal and distal openings to allow the passage of cut bone or tissue therethrough.

Another aspect of the present invention includes a surgical instrument for cutting bone or other tissue which includes a shaft having proximal and distal ends and a longitudinal axis extending between the proximal and distal ends. A cutting head portion is disposed at the distal end of the shaft and includes a first blade having an arcuate configuration to define a distal opening of the instrument. At least one proximal opening is disposed in the cutting head portion and is positioned proximally of the distal opening. The proximal opening includes a second blade disposed along an edge portion thereof. The surgical instrument is configured to cut adjacent bone or tissue with the first blade when the instrument is moved in a forward direction, and is further configured to cut adjacent bone or tissue with the second blade when the instrument is moved in an opposite rearward direction.

Yet another aspect of the present invention includes a surgical instrument for cutting bone or other tissue which includes a shaft having proximal and distal ends and a longitudinal axis extending between the proximal and distal ends. A cutting head portion is disposed at the distal end of the shaft and includes a first blade having an arcuate configuration to define a distal opening of the instrument. A proximal opening is disposed in the cutting head portion and positioned proximally of the distal opening. The proximal opening includes a second blade disposed along an edge portion thereof. The instrument is configured to cut adjacent bone or tissue with the first blade when the instrument is moved in a forward direction, and is further configured to cut adjacent bone or tissue with the second blade when the instrument is moved in an opposite rearward direction. A cylindrical cavity is disposed between the distal opening and the proximal opening for collecting cut bone or tissue during a cutting procedure.

These and other aspects, objects, and features of the present invention will be understood and appreciated by those skilled in the art upon studying the following specification, claims, and appended drawings.

BRIEF DESCRIPTION OF THE DRAWINGS

FIG. 1 is a fragmentary perspective view showing an embodiment of a surgical instrument in accordance with the present invention;

FIG. 2 is a top plan view of the instrument of FIG. 1;

FIG. 3 is a fragmentary right-side view of the instrument of FIG. 1;

FIG. 4 is a distal end view of the instrument of FIG. 1;

FIG. 5 is a fragmentary top plan view of the instrument of FIG. 1;

FIG. 6 is cross-sectional view taken along section line VI of FIG. 5;

FIG. 7 is a perspective view showing a second embodiment of a surgical instrument in accordance with the present invention;

FIG. 8 is a top plan view of the instrument of FIG. 7;

FIG. 9 is a fragmentary right-side view of the instrument of FIG. 7;

FIG. 10 is a distal end view of the instrument of FIG. 7;

FIG. 11 is a fragmentary top plan view of the instrument of FIG. 7;

FIG. 12 is cross-sectional view taken along section line XII of FIG. 11;

FIG. 13 is a side elevational view of an alternate embodiment of a surgical instrument in accordance with the present invention;

FIG. 14 is a top plan view of the instrument of FIG. 13;

FIG. 15 is a side cross-sectional view taken along the section line XV of FIG. 14;

FIG. 16 is an enlarged fragmentary cross-sectional view of the cutting head portion of the instrument of FIG. 15;

FIG. 17 is a distal end view of the instrument of FIG. 13;

FIG. 18 is a fragmentary perspective view of an alternate surgical instrument in accordance with the present invention;

FIG. 19 is a top plan view of the instrument of FIG. 18;

FIG. 20 is a fragmentary right-side view of the instrument of FIG. 18;

FIG. 21 is a distal end view of the instrument of FIG. 18;

FIG. 22 is a fragmentary top plan view of the instrument of FIG. 18;

FIG. 23 is fragmentary cross-sectional view taken along section line XXIII of FIG. 22;

FIG. 24 is a side elevational view of an alternate embodiment of a surgical instrument in accordance with the present invention;

FIG. 25 is a top plan view of the instrument of FIG. 24;

FIG. 26 is a side cross-sectional view taken along the section line XXVI of FIG. 25;

FIG. 27 is an enlarged fragmentary cross-sectional view of the cutting head portion of the instrument of FIG. 26;

FIG. 28 is a distal end view of the instrument of FIG. 24;

FIG. 29A is a side elevational view of a surgical instrument according to another embodiment of the present invention;

FIG. 29B is a fragmentary perspective view of a distal end of the instrument of FIG. 29A;

FIG. 30A is a side elevational view of a surgical instrument according to another embodiment of the present invention;

FIG. 30B is a fragmentary perspective view of a distal end of the instrument of FIG. 30A;

FIG. 31A is a side elevational view of a surgical instrument according to another embodiment of the present invention;

FIG. 31B is a fragmentary perspective view of a distal end of the instrument of FIG. 31A;

FIG. 31C is a fragmentary cross-sectional view taken from line XXXIC of FIG. 31B;

FIG. 33A is a side elevational view of a surgical instrument according to another embodiment of the present invention;

FIG. 33B is a fragmentary perspective view of a distal end of the instrument of FIG. 33A;

FIG. 33C is a cross-sectional view of the instrument of FIG. 33A;

FIG. 36 is a top plan view of a kit having a handle tool along with a number of surgical instruments.

DETAILED DESCRIPTION OF THE PREFERRED EMBODIMENTS

Figure 32A:
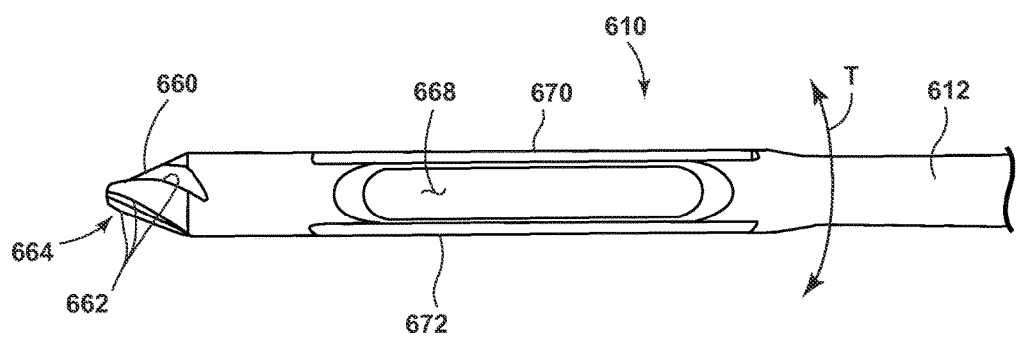
FIG. 32A is a fragmentary top plan view of a distal end of another surgical instrument.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

A surgical instrument 10 in accordance with the present invention is shown in FIGS. 1-6. The instrument 10 is configured for cutting or shaving bone or other tissue, such as for harvesting bone for an autologous bone graft. The instrument 10 includes an elongated shaft portion 12, a distal end 14, and a proximal end 16. The proximal end 16 includes a shank portion 18 configured to be interconnected with a handle or the chuck of a surgical power tool (see FIG. 35), such as an oscillating or reciprocating power tool. At the distal end 14 of the shaft 12, a cutting head portion 20 is disposed. The cutting head portion 20 is enlarged relative to the shaft portion 12 and in this form has a generally conical shape, such that the diameter of the cutting head 20 may increase in the distal direction. At a distal-most end of the cutting head 20, an annular arcuate edge is sharpened to form an annular arcuate blade 22 with no interruptions for cutting bone or other tissue. The arcuate blade 22, in this embodiment has, an elliptical configuration with a major axis M1 that extends laterally across the tool axis and a minor axis m1 that extends along the superior-inferior axis perpendicular to the major axis M1, as shown in FIG. 4. In one form, the transverse width of the arcuate blade 22 at its distal extent along the major axis M1 is approximately 6 mm, and the height along the minor axis m1 is approximately 3 mm. The arcuate blade 22 may take other configurations, such as other elliptical shapes, circular shapes, as shown in FIGS. 13-28, or other arcuate shapes. However the arcuate blade 22 need not be completely arcuate, and in other embodiments, a non-arcuate blade shape may be used (see FIGS. 34A-34B).

The arcuate blade 22 defines a distal opening 24 of the cutting head 20, which lies substantially in a plane that is transverse to the longitudinal axis, and more particularly, is generally perpendicular to the longitudinal axis of the instrument 10. The distal opening 24 is also centered on the longitudinal axis. The cutting head 20 includes at least one proximal opening 26 that lies proximally of the distal opening 24. As shown in FIG. 6, the cutting head 20 includes superior and inferior proximal openings 26, 28 disposed on opposed surfaces of the cutting head 20. The distal opening 24 and the proximal openings 26, 28 are connected via a central channel or passage 30 which allows cut bone or tissue to travel between the openings 24, 26, 28. Lateral arm portions 50, 52 extend from the shaft portion 12 along the lateral sides of the proximal openings 26, 28 and connect the distal arcuate blade 22 to the shaft portion 12. The central channel 30 is formed by the interior surface portions of the cutting head 20, which include a distal inclined arcuate wall 32, which curves around and is sloped relative to the longitudinal axis to form a distal cutting edge 23 of the arcuate blade 22. Intermediate superior and inferior inclined arcuate wall portions 33, 35 are sloped relative to the longitudinal axis transverse to the slope of distal inclined arcuate wall 32, and proximal superior and inferior inclined surfaces 34, 36. The distal inclined arcuate wall 32 slopes toward the longitudinal axis in the proximal direction at an angle of approximately 18.4 degrees, although other angles are contemplated. The intermediate superior and inferior inclined arcuate wall portions 33, 35, slope away from the longitudinal axis in the proximal direction relative to the longitudinal axis at an angle of approximately 49.4 degrees, although other angles are contemplated. Proximal superior and inferior inclined surfaces 34, 36 are inclined with respect the longitudinal axis and each terminates at the superior and inferior openings 26, 28, respectively, for guiding cut bone or tissue between the openings 26, 28. The proximal inclined surfaces 34, 36 can take a variety of configurations, but in one form may be inclined at a range of about 15 degrees to about 35 degrees with respect to the longitudinal axis.

The proximal openings 26, 28 have a generally triangular shape when viewed from the above or below (see FIG. 2), and may be configured with one or more sharpened cutting edge portions along the perimeter of the openings for cutting bone or tissue. Preferably the proximal sharpened cutting edge portions are located along the superior transverse edge portion 38 along the superior opening 26 and similarly along the inferior transverse edge portion 40 along the inferior opening 28. The superior and inferior transverse edge portions 38, 40 are formed, at least in part, at proximal edge portions of the intermediate superior and inferior proximal inclined arcuate wall portions 33, 35. As shown in FIG. 6, the superior and inferior transverse cutting edge portions 38, 40 define second and third blades of the instrument 10 and generally follow the contour of the arcuate blade 22 along their length. Accordingly, the cutting head portion 20 may be configured for cutting in at least two directions, specifically in the distal and proximal directions or forward and rearward directions. With this configuration, the cutting head 20 will cut adjacent tissue or bone with the distal arcuate blade 22 when the instrument is moved distally or in a forward direction. Further, the instrument 10 will cut with at least one of the superior and inferior transverse cutting edge portions 38, 40 when the instrument 10 is moved proximally or in an opposite rearward direction. Such an arrangement is particularly advantageous when the instrument 10 is attached to a reciprocating power tool configured to shift or oscillate the cutting head 20 back and forth for quickly and accurately removing bone or tissue in both directions of a stroke of the cutting head 20.

In use, as the arcuate blade 22 is advanced distally along bone or tissue to cut, shave or otherwise remove pieces of the bone or tissue with the arcuate blade 22 (the first blade). Cut pieces of bone or tissue will enter the distal opening 24, travel through the central channel 30 and then exit through either the superior or inferior proximal opening 26, 28. The cut pieces may then be collected for testing, use as bone graft material or discarded. When the instrument 10 is provided with proximal cutting edge portions 38, 40 (second and third blades), cut bone will travel the opposite direction in a rearward movement of the instrument 10 and exit from the distal opening 24, or in some cases the opposite proximal opening 26, 28 from the side of the cutting head that is performing a cutting action.

The shank portion 18 may take a variety of configurations for mating with a handle or grip for manual operation of the instrument, or alternatively with the chuck of a power tool. As shown in FIGS. 1-3, the shank portion 18 may have a plurality of scalloped portions 42 on the superior and inferior surfaces of the proximal portion 16 of the shaft 12 for improved grip with the mating portion of the handle or power tool. Other configurations of the shank portion 18 may be used for connecting the instrument to a handle or tool, as will be apparent to one of ordinary skill.

Another surgical instrument 110 according to the present invention is shown in FIGS. 7-12. The instrument 110 is similar to the instrument 10 disclosed in FIGS. 1-6, except the instrument 110 is provided with a single proximal opening 126 on a superior portion of the cutting head 120 instead of having two proximal openings 26, 28 opposite one another. Similar portions of the tool in FIGS. 7-12 to those of the tool shown in FIGS. 1-6 are labeled with similar numbering, except for the addition of 100, e.g., the cutting head portion 20 is labeled 120 in FIGS. 7-12. For the sake of brevity, description of similar portions of the instrument shown in FIGS. 7-12 is omitted, and reference may be made to the description provided above for the instrument 10.

As best shown in FIG. 12, the central passage or channel 130 has a slightly different configuration from the central passage 30 shown in FIG. 6 given that there is only a single proximal opening 126. The central channel 130 is formed by the interior surface portions of the cutting head 120, which include a distal inclined arcuate wall 132, which forms distal cutting edge 123 of the arcuate blade 122, and a proximal inclined surface 134. The distal inclined arcuate wall 132 slopes toward the longitudinal axis in the proximal direction at an angle of approximately 18.4 degrees with respect to the longitudinal axis, although other angles are contemplated. The central channel 130 is also formed in part by an intermediate superior inclined arcuate wall portion 133, which is sloped relative to the longitudinal axis and transverse to the slope of distal inclined arcuate wall 132, and forms superior transverse cutting edge 138 at a proximal portion of the intermediate superior inclined arcuate wall portion 133. The intermediate superior inclined arcuate wall portion 133 slopes away from the longitudinal axis in the proximal direction at an angle of approximately 31.4 degrees relative to the longitudinal axis, although other angles are contemplated. The inclined surface 134 is inclined with respect the longitudinal axis and terminates at the superior opening 126 for guiding cut bone or tissue from arcuate blade 122 to the superior opening 126. The inclined surface 134 can take a variety of configurations, but in one form may be inclined at a range of about 15 degrees to about 35 degrees with respect to the longitudinal axis. Similar to the instrument 10 disclosed in FIGS. 1-6, the instant instrument 110 may be used in a reciprocating fashion for cutting bone or tissue when the instrument 110 is shifted both distally and proximally.

Another surgical instrument 210 according to the present invention is shown in FIGS. 13-17. The instrument 210 is similar to the instrument 10 disclosed in FIGS. 1-6, except that the instrument 210 includes a distal arcuate blade 222 having a circular configuration (see FIG. 17), rather than an elliptical configuration. Similar portions of the instrument 210 in FIGS. 13-17 to those of the instrument 10 shown in FIGS. 1-6 are labeled with similar numbering, except for the addition of 200, e.g., the cutting head portion 20 is labeled 220 in FIGS. 13-17. For the sake of brevity, description of similar portions of the instrument 210 shown in FIGS. 13-17 will be omitted, but reference may be made to the description above with respect to the embodiment of the instrument 10 shown in FIGS. 1-6.

The cutting head 220 is formed with a distal opening 224 and proximal openings 226, 228, similar to the cutting head 20 shown in FIG. 6. The proximal openings 226, 228 are provided with sharpened cutting edge portions 238, 240 along the perimeter of the openings for cutting bone or tissue. The proximal sharpened cutting edge portions 238, 240 are located along the superior transverse edge portion along the superior opening 226 and similarly along the inferior transverse edge portion along the inferior opening 228. As shown in FIG. 16, the superior and inferior transverse cutting edge portions 238, 240 generally follow the contour of the arcuate blade 222 along their length. Accordingly, the cutting head portion 220 is configured for cutting in at least two directions, specifically in the distal and proximal directions. The cutting head 220 is configured to cut adjacent tissue or bone with the distal arcuate blade 222 when the instrument 210 is shifted distally and will cut adjacent tissue or bone with the proximal sharpened cutting edge portions 238, 240 on the transverse edge portions 238, 240 when the instrument 210 is shifted proximally.

In the disclosed form, the cutting head 220 is contemplated to have an outer diameter of 10 mm, while the shaft 212 is contemplated to have an outer diameter of 6 mm. The superior and inferior proximal openings 226, 228 have a generally teardrop or egg shape when viewed from above or below, and are circumscribed, at least in part, by superior and inferior inclined surfaces 234, 236. In a preferred form, the openings 226, 228 have a width of approximately 7.5 mm. The superior and inferior inclined surfaces 234, 236 are inclined with respect the longitudinal axis for guiding cut bone or tissue between the openings through channel 230. The inclined surfaces 234, 236 can take a variety of configurations, but in one form may be inclined at an angle α, which falls within a range of about 15 degrees to about 35 degrees with respect to the longitudinal axis. The incline of the distal inclined arcuate wall, which forms cutting edge 223, with respect to the longitudinal axis is shown as the angle β in FIG. 15. Naturally, this angle β can vary depending on the desired sharpness and durability of the blade, but in a preferred form falls preferably in a range of about 10 degrees to about 30 degrees. It is further contemplated that the cutting head 220 may include an outer diameter in a range from about 5 mm to about 15 mm.

The shank portion 218 of the instrument 210 has a flat portion 244 on the superior distal end 216 of the shaft 212 for indexing and engaging with a handle or power tool. In addition, the shank portion 218 includes a recessed portion or groove 246 spaced from the proximal end of the shaft 212 for engaging with a corresponding biased ball or other similar structure of the handle or tool for temporarily attaching the handle or tool to the instrument shank 218.

Another surgical instrument 310 according to the present invention is shown in FIGS. 18-23. The instrument 310 is similar to the instrument 210 disclosed in FIGS. 13-17, except that that the cutting head portion 320 is larger relative to the shaft 312 compared with the cutting head portion 220 and shaft 212 of instrument 210. Similar portions of the instrument 310 in FIGS. 18-23 to those of the instrument 10 shown in FIGS. 1-6 are labeled with similar numbering, except for the addition of 300, e.g., the cutting head portion 20 is labeled 320 in FIGS. 18-23. For the sake of brevity, description of similar portions of the instrument 310 shown in FIGS. 18-23 will be omitted, but reference may be made to the description above.

The proximal openings 326, 328 have a shape similar to the generally triangle shape of the openings 26, 28 in FIG. 5, but the sides are more rounded. In addition, the superior and inferior interior inclined wall portions 334, 336 have a wider contour that follows the larger cutting head portion 320 size. The distal inclined arcuate wall 332 slopes toward the longitudinal axis in the proximal direction at an angle of approximately 34 degrees with respect to the longitudinal axis, although other angles are contemplated. The central channel 330 is also formed in part by intermediate superior and inferior inclined arcuate wall portions 333, 335 which are sloped relative to the longitudinal axis and transverse to the slope of distal inclined arcuate wall 332. The superior and inferior transverse cutting edges 338, 340 further define the central channel 330 at proximal portions of the intermediate superior inclined arcuate wall portions 333, 335. The intermediate superior inclined arcuate wall portions 333, 335 slope away from the longitudinal axis in the proximal direction at an angle of approximately 26 degrees relative to the longitudinal axis, although other angles are contemplated. The shank portion 318 has a similar scalloped configuration to the instruments 10, 110 disclosed in FIGS. 1-12.

Another surgical instrument 410 according to the present invention is shown in FIGS. 24-28. The instrument 410 is similar to the instruments 110, 210 disclosed in FIGS. 7-12 and 13-17, except that the cutting head portion 420 has a different configuration. In particular, the cutting head 420 has a diameter roughly the same size or slightly smaller than the diameter of the shaft 412. For example, in the disclosed embodiment, the cutting head portion 420 may have an outer diameter of 4 mm, while the shaft 412 may have an outer diameter of 4.5 mm. In addition, the cutting head portion 420 is elongated, such that the distance between the distal opening 424 and the superior proximal opening 426 is greater compared to other embodiments disclosed herein. Similar portions of the instrument 410 shown in FIGS. 18-23 to those of the instrument 10 shown in FIGS. 1-6 are labeled with similar numbering, except for the addition of 400, e.g., the cutting head portion 20 is labeled 420 in FIGS. 24-28. For the sake of brevity, description of similar portions of the instrument 410 shown in FIGS. 24-28 will be omitted, but reference may be made to the description above.

As shown in FIG. 27, the cutting head 420 includes an elongate central passage 430 that extends between the distal opening and the proximal opening 426 for collecting cut bone or tissue from the distal cutting edge 422, or alternatively transferring cut bone or tissue from the distal cutting edge 422 to the proximal opening 426, should sufficient bone or tissue be cut and collected in the central passage 430 such that newly cut bone or tissue entering the distal opening 424 pushes the collected bone or tissue nearest the proximal end of the central passage 430 out of the proximal opening 426. The proximal opening 426 has a generally teardrop or egg shape when viewed from above, and in the disclosed form, has a width of approximately 3 mm. The proximal opening 426 may include a superior transverse cutting edge portion 438 for cutting bone or tissue when the cutting head 420 is shifted proximally with respect to adjacent bone or tissue. A proximal inclined interior surface portion 434 is oriented at an angle α with respect to the longitudinal axis, which angle can take on a range of values, but is preferably between 10-50 degrees, and in the disclosed embodiment is approximately 20 degrees. The shank portion 418 is identical to the shank portion 218 of instrument 210 shown in FIG. 13, which allows the instrument 410 to be connected to a handle or a power tool.

Referring now to FIG. 29A, an instrument 10A is shown similar to instrument 10 shown and described above with reference to FIGS. 1-6. Instrument 10A includes a shaft portion 12 having both a distal end 14 and proximal end 16. The proximal end 16 of instrument 10A includes a shank portion 18 which is similar to shank portion 218 of the instrument 210 shown and described above with reference to FIGS. 13-17. As such, the shank portion 18 of the instrument 10A includes a flat portion 244A and a recessed portion or groove 246A for engaging a handle or tool in a releasable manner when using the instrument 10A. As shown in FIG. 29B, the distal end 14 of the instrument 10A includes a similar configuration to the instrument 10 shown and described above with reference to FIGS. 1-6, except that the arcuate blade 22 of instrument 10A has a generally circular configuration as compared to the elliptical or oval configuration of the arcuate blade 22 of instrument 10.

Referring now to FIG. 30A, an instrument 110A is shown similar to instrument 110 described above with reference to FIGS. 7-12. The instrument 110A includes an elongate shaft 112 having both a distal end 114 and a proximal end 116. The proximal end 116 includes a shank 118 similar to shank 18 described above with reference to instrument 10A. Referring now to FIG. 30B, the distal end 114 of the instrument 110A includes a configuration similar to the distal end 114 of instrument 110 described above with reference to FIGS. 7-12, except that the arcuate blade 122 of instrument 110A has a generally circular configuration as compared to the elliptical or oval configuration of the arcuate blade 122 of instrument 110.

Another surgical instrument 510 according to the present invention is shown in FIGS. 31A-31C. The instrument 510 is similar to the instrument 10 disclosed in FIGS. 1-6, except that instrument 510 includes a distal end 514 having an elongate circular configuration. Similar portions of the instrument 510 shown in FIGS. 31A-31C as compared to instrument 10 shown in FIGS. 1-6 are labeled with similar numbering, except for the addition of 500, e.g., the cutting head portion 20 is labeled 520 in FIGS. 31A-31C. For the sake of brevity, description of similar portions of the instrument 510 shown in FIGS. 31A-31C will be omitted, but reference may be made to the description above with respect to the embodiment of FIGS. 1-6.

With further reference to FIGS. 31A-31C, the cutting head 520 of instrument 510 is formed with a distal opening 524 and proximal openings 526, 528, similar to the cutting head 20 shown in FIG. 6. The proximal openings 526, 528 are provided with sharpened cutting edge portions 538, 540 along the perimeter of the openings for cutting bone or tissue. The proximal sharpened cutting edge portions 538, 540 are located along the superior transverse edge portion along the superior opening 526 and similarly along the inferior transverse edge portion along the inferior opening 528. As best shown in FIG. 31C, the superior and inferior transverse cutting edge portions 538, 540 are spaced apart from the cutting head 522 by a generally cylindrical body portion 560 having an exterior wall 562 defining a cavity 530. Cavity 530 is akin to central channel 30 of the instrument 10 disclosed in FIGS. 1-6, but is spaced apart between distal opening 524 and proximal openings 526, 528 to form an elongate cavity 530. Thus, cavity 530 can be used to collect and retain bone and tissue cut by the instrument 510 at the arcuate cutting blade 522 or the superior and inferior transverse cutting edge portions 538, 540 (depending on the direction of the cutting action of the instrument 510). For example, instrument 510 can cut bone or tissue from the distal cutting edge 522 to the proximal opening 526 along the path as indicated by arrow A. Should sufficient bone or tissue be cut and collected in the cavity 530, that material can be collected, or newly cut bone or tissue entering the distal opening 524 and cavity 530 can push the collected bone or tissue through the cavity 530 and out one of the proximal openings 526, 528.

Figure 32B:
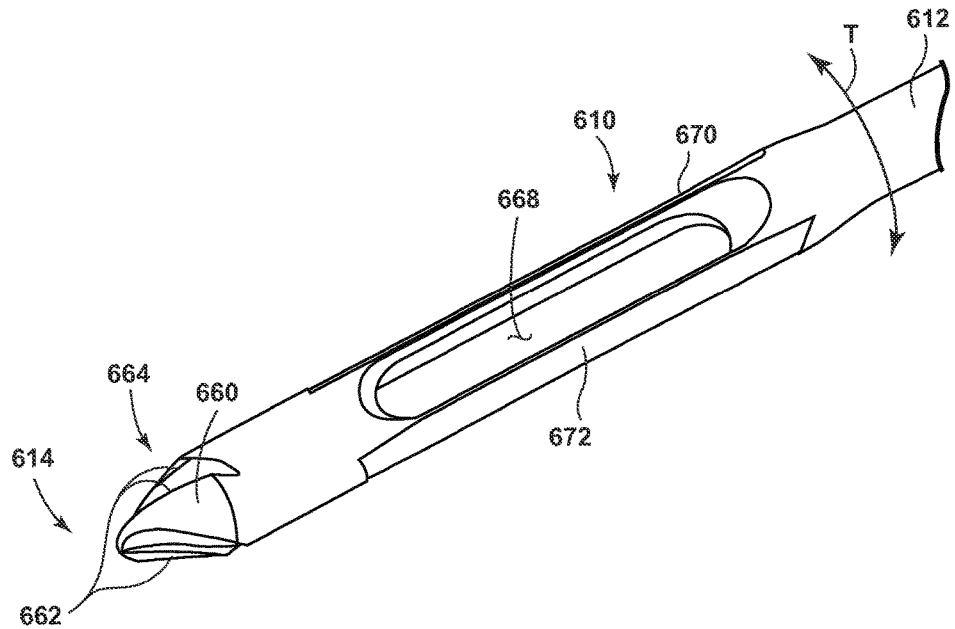
FIG. 32B is a fragmentary perspective view of the distal end of the instrument of FIG. 32A.

Referring now to FIGS. 32A and 32B, a distal end 614 of another surgical instrument 610 is shown. The instrument 610 is contemplated to have a shaft and shank portion similar to the shaft 12 and shank portion 18 found on instrument 10 as disclosed in FIGS. 1-6. The distal end 614 of instrument 610 includes a conical shaped distal-most portion 660 having a number of flutes 662. The flutes 662 are spiral shaped flutes having sharpened blades disposed around the conical shaped distal-most portion 660 to define a reamer end 664 for cutting or shaving bone or tissue when the instrument 610 is twisted or rotated as indicated by arrow T. Disposed proximally from the reamer end 664, a through aperture 668 is formed through the shaft 612 of the instrument 610. It is contemplated that the through aperture 668 is disposed about 3 mm from the reamer end 664 of the instrument 610, but may be placed any distance from the reamer end 664. It is contemplated that the through aperture 668 is configured to store bone and tissue that is reamed by the reamer end 664 of instrument 610 for collection and use in a subsequent procedure (i.e. bone grafting). The through aperture 668 is generally defined by sidewalls 670, 672, disposed on opposite sides thereof, which may be substantially flat sidewalls as best shown in FIG. 32B.

Referring now to FIGS. 33A-33C, another surgical instrument 710 is shown. The instrument 710 is shown having a distal end 714 and proximal end 716 along with a shaft 712 and shank portion 718 similar to the component parts found on instrument 10 as disclosed in FIGS. 1-6. The distal end 714 of instrument 710 includes a conical shaped distal-most portion 760 having a number of flutes 762 extending rearwardly therefrom. The flutes 762 are spiral shaped flutes having sharpened blades disposed around the conical shaped distal-most portion 760 to define a reamer end 764 for cutting or shaving bone or tissue when the instrument 610 is twisted or rotated as indicated by arrow T. A narrowed portion 766 of the instrument 710 separates the reamer end 764 from the shaft 712, such that the reamer end 764 has a larger diameter as compared to the shaft 712. As best shown in FIG. 33C, the instrument 710 is a cannulated instrument having a centrally disposed cannula 770 with opposite openings 772 and 774 disposed at the distal end 714 and proximal end 716, respectively. In use, a guide wire GW (FIG. 33B) can be pinned in place in an area to be reamed, such as a vertebrae disposed along a spinal column of a patient, and the guide wire GW can then be received in the centrally disposed cannula 770 through distal end opening 772 for guiding the instrument 710 during a reaming procedure.

Figure 34B:
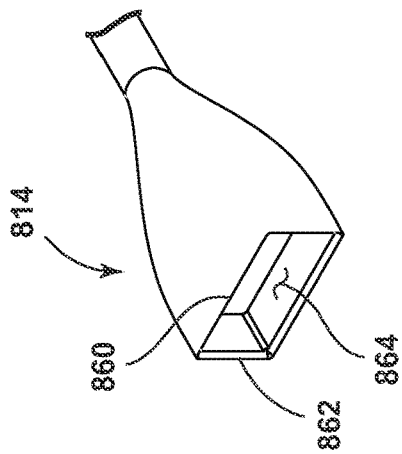
FIG. 34B is a fragmentary perspective view of a distal end of the instrument of FIG. 34A.
Figure 34A:
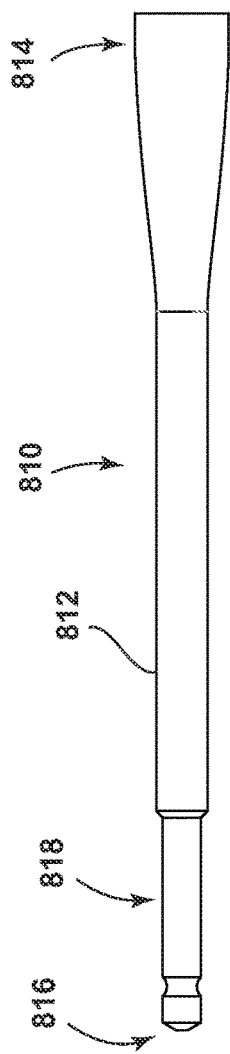
FIG. 34A is a side elevational view of a surgical instrument according to another embodiment.

Referring now to FIGS. 34A and 34B, another surgical instrument 810 is shown. The instrument 810 is shown having a distal end 814 and proximal end 816 along with a shaft 812 and shank portion 818 similar to the component parts found on instrument 10 as disclosed in FIGS. 1-6. The distal end 814 of instrument 810 includes a rectangular-shaped distal-most portion 860 having a blade 862 extending around a perimeter thereof. The blade 862 is contemplated for use in cutting or shaving bone or tissue A rectangular-shaped cavity 864 of the instrument 810 is disposed proximally from the blade 862 and is configured to collect bone or tissue cut by the blade 862 during a surgical procedure.

Figure 35:
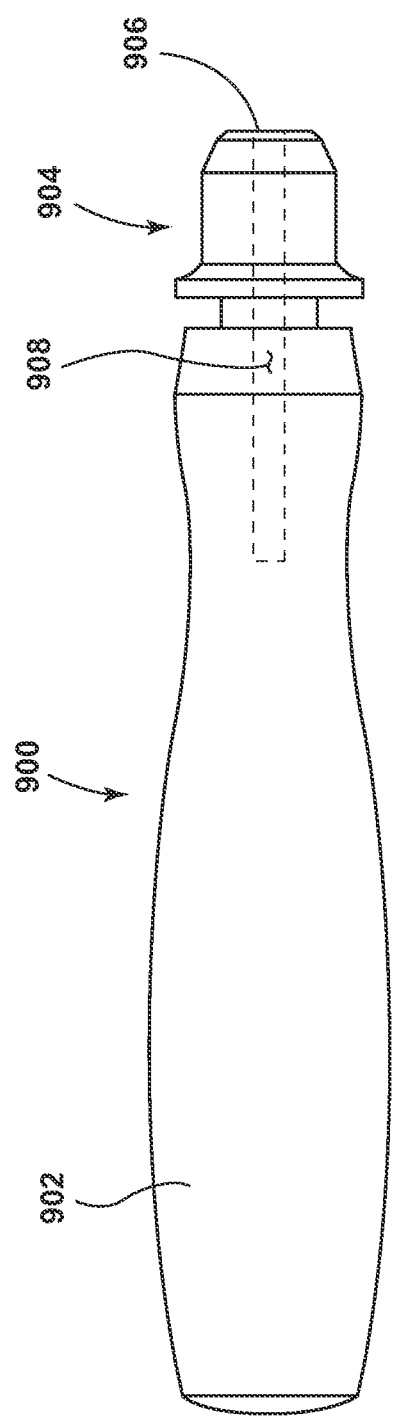
FIG. 35 is a top plan view of a handle tool for use in conjunction with the present invention.

Referring now to FIG. 35, a surgical tool 900 is shown for use with any of the instruments of the present invention. The tool 900 includes a handle portion 902 and a connection end 904. The connection end 904 includes a distal aperture 906 opening into a receiving channel 908. In use, the shank portion of an instrument is contemplated to be received through distal aperture 906 and into receiving channel 908. In this way, the tool 900 can be used to connect to and operate a surgical instrument, such as surgical instrument 10 shown and described above. The connection end 904 may be a quick release end with a biasing ball or other like connection known in the art. With reference to FIG. 36, the tool 900 is shown as part of a kit 910, wherein the kit 910 depicted in FIG. 36 includes a number of surgical instruments 10, 110, 510 and 610 displayed on a sterilization grate 912. The tool 900 is contemplated for use with the surgical instruments 10, 110, 510 and 610 shown in FIG. 36 and it is further contemplated that the kit 910 can be customized with any surgical instruments specific for use during a given procedure.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the invention as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present invention. The exemplary structures and processes disclosed herein are for illustrative purposes and are not to be construed as limiting.

It is also to be understood that variations and modifications can be made on the aforementioned structures and methods without departing from the concepts of the present invention, and further it is to be understood that such concepts are intended to be covered by the following claims unless these claims by their language expressly state otherwise.

While the invention has been described with respect to specific examples including presently preferred modes of carrying out the invention, those skilled in the art will appreciate that there are numerous variations and permutations of the above described systems and techniques that fall within the spirit and scope of the invention as set forth in the claims.

The invention claimed is:

1. A surgical instrument for cutting bone or other tissue, comprising:
   a shaft portion having proximal and distal ends and a longitudinal axis extending between the proximal and distal ends;
   a cutting head portion at the distal end of the shaft portion having an arcuate blade at a distal most end of the cutting head portion which defines a distal opening that lies substantially in a plane that is transverse to the longitudinal axis;

a proximal opening in the cutting head portion located proximally of the arcuate blade;
a central channel that connects the proximal and distal openings to allow the passage of cut bone or tissue therethrough; and
a first interior surface portion extending inwardly into the central channel from the arcuate blade at a first angle, and a second interior surface portion extending outwardly at a second angle from an innermost portion of the first interior surface portion, wherein the second interior surface culminates in a sharpened edge portion at an outermost portion thereof, and further wherein the sharpened edge portion is disposed proximally to the arcuate blade.

2. The surgical instrument of claim 1, wherein the arcuate blade has an elliptical configuration.

3. The surgical instrument of claim 1, wherein the arcuate blade has a circular configuration.

4. The surgical instrument of claim 1, wherein the distal opening is centered on the longitudinal axis of the shaft portion.

5. The surgical instrument of claim 1, including:
a third interior surface portion extending into the central channel from the distal end of the shaft portion, wherein the third interior surface portion is outwardly inclined with respect to the longitudinal axis, and further wherein the third interior surface portion includes a proximal edge that terminates at the proximal opening for guiding cut bone or tissue therealong.

6. The surgical instrument of claim 5, including:
a second proximal opening located proximally of the arcuate blade and connected to the distal opening via the central channel; such that the cut bone or tissue may pass through the central channel and through either or both of the first proximal opening and the second proximal opening.

7. The surgical instrument of claim 6, including:
a fourth interior surface portion extending into the central channel from the distal end of the shaft portion, wherein the fourth interior surface portion is outwardly inclined with respect to the longitudinal axis, and further wherein the fourth interior surface includes a proximal edge that terminates at the proximal opening for guiding cut bone or tissue therealong.

8. The surgical instrument of claim 7, wherein the third and fourth interior surface portions are outwardly inclined in opposite directions with respect to the longitudinal axis and diverge apart from one another as they extend proximally.

9. The surgical instrument of claim 6, wherein the first and second proximal openings each comprise a sharpened edge portion for cutting bone or tissue.

10. The surgical instrument of claim 9, wherein each of the sharpened edge portions are oriented to cut adjacent tissue or bone when the instrument is shifted proximally.

11. The surgical instrument of claim 1, wherein the sharpened edge portion is oriented to cut adjacent tissue or bone when the instrument is shifted proximally.

12. A surgical instrument for cutting bone or other tissue, comprising:
a shaft having proximal and distal ends and a longitudinal axis extending between the proximal and distal ends;
a cutting head portion disposed at the distal end of the shaft, wherein the cutting head portion includes a first blade having an arcuate configuration to define a distal opening of the instrument;
at least one proximal opening disposed in the cutting head portion and positioned proximally of the distal opening, wherein the at least one proximal opening includes a second blade having a sharpened edge portion disposed along an edge portion of the proximal opening, wherein the instrument is configured to cut adjacent bone or tissue with the first blade when the instrument is moved in a forward direction, and further wherein the instrument is configured to cut adjacent bone or tissue with the second blade when the instrument is moved in an opposite rearward direction; and
an interior surface having a first portion extending inwardly from the arcuate blade towards the longitudinal axis, and a second portion extending outwardly away from the longitudinal axis, wherein the second portion culminates in the sharpened edge portion of the second blade.

13. The surgical instrument of claim 12, including:
a central channel that extends between the at least one proximal opening and the distal opening, wherein the central channel is configured to allow cut bone or tissue to pass therethrough.

14. The surgical instrument of claim 13, wherein the at least one proximal opening includes first and second proximal openings disposed through opposite surfaces of the cutting head portion, and further wherein the first and second proximal openings open into the central channel, such that the cut bone or tissue may pass through the central channel and through either or both of the first and second proximal openings from the distal opening.

15. The surgical instrument of claim 14, wherein the second proximal opening includes a third blade disposed along an edge portion thereof.

16. The surgical instrument of claim 12, wherein the arcuate configuration of the first blade includes a radius within a range from about 5 mm to about 15 mm.

17. A surgical instrument for cutting bone or other tissue, comprising:
a shaft having proximal and distal ends and a longitudinal axis extending between the proximal and distal ends;
a cutting head portion disposed at the distal end of the shaft, wherein the cutting head portion includes a first blade having an arcuate configuration to define a distal opening of the instrument;
a proximal opening disposed in the cutting head portion and positioned proximally of the distal opening, wherein the proximal opening includes a second blade disposed along an edge portion thereof, wherein the instrument is configured to cut adjacent bone or tissue with the first blade when the instrument is moved in a forward direction, and further wherein the instrument is configured to cut adjacent bone or tissue with the second blade when the instrument is moved in an opposite rearward direction;
a cylindrical cavity disposed between the distal opening and the proximal opening for collecting cut bone or tissue; and
an interior surface having a first portion extending inwardly from the arcuate blade into the cavity, and a second portion extending outwardly from the cavity, wherein the second portion culminates in the sharpened edge portion of the second blade.

18. The instrument of claim 17, wherein the proximal end includes a shank portion configured to matingly engage with a tool for actuating the instrument.

19. The surgical instrument of claim 18, wherein the first portion and the second portion of the interior surface converge at a point within the cavity.

* * * * *

UNITED STATES PATENT AND TRADEMARK OFFICE
CERTIFICATE OF CORRECTION

PATENT NO. : 9,974,548 B2  
APPLICATION NO. : 14/848893  
DATED : May 22, 2018  
INVENTOR(S) : Russo et al.

Page 1 of 1

It is certified that error appears in the above-identified patent and that said Letters Patent is hereby corrected as shown below:

Column 9  
Line 38, "α" should be -- γ --.

Column 13  
Claim 6, Line 33, ";" should be -- , --.

Column 13  
Claim 7, Line 43, After "the" insert -- second --.

Signed and Sealed this  
Twenty-first Day of August, 2018

Andrei Iancu  
*Director of the United States Patent and Trademark Office*